US011542243B1

(12) United States Patent
Jones et al.

(10) Patent No.: US 11,542,243 B1
(45) Date of Patent: Jan. 3, 2023

(54) METHOD OF CONVERTING DELTA9-THC TO DELTA10-THC AND THE PURIFICATION OF THE DELTA10-THC BY CRYSTALLIZATION

(71) Applicant: FusionFarms, LLC, Adelanto, CA (US)

(72) Inventors: Joshua Jones, Englewood, CO (US); Justin Cotham, Canyon Lake, CA (US); Nicholas Frilot, Corona, CA (US)

(*) Notice: Subject to any disclaimer, the term of this patent is extended or adjusted under 35 U.S.C. 154(b) by 278 days.

(21) Appl. No.: 17/035,396

(22) Filed: Sep. 28, 2020

Related U.S. Application Data

(60) Provisional application No. 62/906,320, filed on Sep. 26, 2019.

(51) Int. Cl.
| | | |
|---|---|---|
| C07D 311/80 | (2006.01) | |
| B01D 3/10 | (2006.01) | |
| B01D 11/02 | (2006.01) | |
| B01D 3/14 | (2006.01) | |
| B01D 15/08 | (2006.01) | |
| G01N 30/86 | (2006.01) | |

(Continued)

(52) U.S. Cl.
CPC .............. *C07D 311/80* (2013.01); *B01D 3/10* (2013.01); *B01D 3/143* (2013.01); *B01D 9/0059* (2013.01); *B01D 11/0296* (2013.01); *B01D 15/08* (2013.01); *G01N 30/86* (2013.01); *B01D 2009/0086* (2013.01); *G01N 2030/027* (2013.01)

(58) Field of Classification Search
None
See application file for complete search history.

(56) References Cited

U.S. PATENT DOCUMENTS

| | | | |
|---|---|---|---|
| 2003/0017216 A1* | 1/2003 | Schmidt | A61K 36/185 424/725 |
| 2004/0049059 A1 | 3/2004 | Mueller | |
| 2004/0143126 A1 | 7/2004 | Webster et al. | |

(Continued)

FOREIGN PATENT DOCUMENTS

| | | |
|---|---|---|
| WO | 2009/099868 A1 | 8/2009 |
| WO | 2018/015886 A1 | 1/2018 |

(Continued)

*Primary Examiner* — Tam M Nguyen
(74) *Attorney, Agent, or Firm* — JRG Attorneys at Law (57) ABSTRACT

A method of isomerizing Δ9-tetrahydrocannabinol ("Δ9-THC") to Δ10-tetrahydrocannabinol ("Δ10-THC"). The method includes the steps of: extracting Δ9-THC from cannabis biomass, which optionally contains one or more of the components found in fire retardant such as PHOS-CHEK®; dewaxing of crude extracts by winterization; pH-adjusting extracts by washing the extracts in heptane solution with aqueous solutions of: citric acid, sodium bicarbonate, and brine; isomerizing Δ9-THC to Δ10-THC by exposure to suitable conditions and in the presence of a catalyst based on the components of fire retardant; vacuum distillation of Δ10-THC at a predetermined temperature range and vacuum level; collecting the distillate and redistilling it up to three times to acquire distillate containing less than 60% Δ10-THC; and purification of the MO-THC to a purity of 99% or greater by crystallization from n-pentane solution.

21 Claims, 5 Drawing Sheets

(51) Int. Cl.
*B01D 9/00* (2006.01)
*G01N 30/02* (2006.01)

(56) References Cited

U.S. PATENT DOCUMENTS

| | | |
|---|---|---|
| 2004/0248970 A1 | 12/2004 | Webster et al. |
| 2007/0072939 A1 | 3/2007 | Kupper |
| 2007/0093665 A1* | 4/2007 | Burdick .................. C07C 29/00 |
| | | 549/390 |
| 2009/0298930 A1 | 12/2009 | Gutman et al. |
| 2010/0298579 A1 | 11/2010 | Steup et al. |
| 2012/0202891 A1 | 8/2012 | Stinchcomb et al. |
| 2013/0067619 A1 | 3/2013 | Page et al. |
| 2013/0089600 A1 | 4/2013 | Winnicki |
| 2014/0271940 A1 | 9/2014 | Wurzer |
| 2015/0152018 A1* | 6/2015 | Raber .................. C07B 63/00 |
| | | 549/390 |
| 2016/0045471 A1 | 2/2016 | Stodola |
| 2016/0250270 A1 | 9/2016 | Wendschuh et al. |
| 2016/0326130 A1 | 11/2016 | Changoer et al. |
| 2017/0008868 A1 | 1/2017 | Dialer et al. |
| 2017/0008870 A1 | 1/2017 | Dibble et al. |
| 2017/0021029 A1* | 1/2017 | Raber ...................... A61K 9/12 |
| 2017/0172977 A1 | 6/2017 | Kleidon et al. |
| 2018/0237368 A1 | 8/2018 | Keller |
| 2019/0046499 A1 | 2/2019 | Segretti |
| 2019/0144414 A1 | 5/2019 | Erfurt et al. |
| 2019/0151280 A1 | 5/2019 | Eades et al. |
| 2019/0247325 A1 | 8/2019 | Kleidon |
| 2020/0262806 A1* | 8/2020 | Webb .................... C07C 37/004 |

FOREIGN PATENT DOCUMENTS

| | | |
|---|---|---|
| WO | 2018/061007 A1 | 4/2018 |
| WO | 2019/046850 | 3/2019 |

* cited by examiner

'Δ10-THC'

METHOD OF CONVERTING DELTA9-THC TO DELTA10-THC AND THE PURIFICATION OF THE DELTA10-THC BY CRYSTALLIZATION

PRIORITY CLAIM

This non-provisional application claims priority to provisional patent application Ser. No. 62/906,320, entitled "Method of Converting Delta9-THC to Delta10-THC and the Purification of the Delta10-THC by Crystallization", filed on Sep. 26, 2019.

TECHNICAL FIELD

The present invention relates generally to processes for the extraction, refinement and distillation of cannabis extracts, and more specifically, but not limited to, a method of isomerizing Δ9-tetrahydrocannabinol ("Δ9-THC") to Δ10-tetrahydrocannabinol ("Δ10-THC").

BACKGROUND OF THE INVENTION

The *Cannabis sativa* plant is the primary source of cannabinoids. Cannabinoids are a diverse class of chemical compounds that act as ligands to the endocannabinoid receptors. Cannabinoids offer a variety of pharmacological benefits, including, but not limited to, anti-spasmodic, anti-convulsant, anti-psychotic, anti-oxidant, neuroprotective, anti-inflammatory, anti-cancer, and immunomodulatory effects.

Δ9-THC, which stands for Δ9-tetrahydrocannabinol, and is synonymous with the terms (6aR,10aR)-delta-9-tetrahydrocannabinol, and (—)-trans-Δ$^9$-tetrahydrocannabinol, is one cannabinoid molecule found in marijuana (cannabis) that's long been recognized as its main psychoactive ingredient that is, the substance that causes users to experience the marijuana high. In fact, Δ9-THC is just one of more than 400 different substances and 60 different cannabinoid molecules contained in marijuana, although Δ9-THC is the most recognized.

Various processes have been made to extract and purify Δ9-THC and other constituents present in cannabis plants in order to separate and isolate these unique compounds. These techniques often involve the use of pressurized and explosive hydrocarbons, or pressurized carbon dioxide, each of which presents hazards to human operators and equipment. Typically, these extraction and refining techniques aim to avoid isomerization of double bonds in cannabinoids, although processes have been made to isomerize Δ9-THC to Δ8-THC.

Isomerization of Δ9-THC to Δ10-THC has been previously reported through the stoichiometric use of highly toxic and pyrophoric reagents such as n-butyl lithium, which can be costly and tedious and are not appropriate for use in the newly state-legalized cannabis markets, which do not allow use of these dangerous reagents in production scenarios. In addition, chromatographic separation techniques have been used for purifying the resulting reaction products in the reported methods for isomerizing Δ9-THC to Δ10-THC, which is also costly and tedious, and may fall outside the scope of cannabis production facilities operating within the frameworks of state-legalized cannabis.

In light of the shortcomings in the prior art, there is clearly a need for a safe, simple, and easy way to produce Δ10-THC that uses manageable quantities of safe components, and that advantageously avoids costly and tedious separation techniques.

SUMMARY OF THE INVENTION

The present invention relates to a method of achieving a specific and high-yielding isomerization of Δ9-THC to Δ10-THC.

Another aspect of the present invention is to provide a method of purifying Δ10-THC up to 99% purity without the use of chromatography.

A further aspect of the present invention is to efficiently shift the Δ9 bond in Δ9-THC to the MO position to produce Δ10-THC.

Another feature of the present invention is a technique for isomerizing Δ9-THC to MO-THC in the presence of catalytic amounts of elemental sulfur and one or more of the compounds found in fire retardant (e.g., PHOS-CHEK®), and exposed to appropriate conditions of temperature, atmosphere and time.

An additional feature of the present invention is to provide a way of producing Δ10-THC in a safe and efficient manner.

One advantage of the present invention is that the process (or similar process) for isomerization of Δ9-THC to Δ10-THC uses catalytic quantities of safe and non-toxic components.

Another embodiment of the present invention includes methods for purification of Δ10-THC by crystallization from various solvents, including n-pentane, for the purpose of avoiding costly and tedious chromatographic separations.

For a better understanding of the present invention, its functional advantages and the specific objects attained by its uses, reference should be made to the accompanying drawings, claims and descriptive matter in which there are illustrated embodiments of the invention.

DETAILED DESCRIPTION

Introduction

In one embodiment, a method of producing Δ10-Tetrahydrocannabinol ("Δ10-THC") by isomerization of Δ9-tetrahydrocannabinol ("Δ9-THC") to Δ10-THC is disclosed. The method includes the steps of: extracting Δ9-THC from a harvested cannabis biomass, the biomass containing elemental sulfur and one or more of the compounds found in commercial fire retardant (e.g., PHOS-CHEK®); dewaxing the crude extracts of cannabis biomass by winterization; dissolving the dewaxed extracts in heptane; adjusting the pH of the dewaxed extracts by washing the heptane solution of dewaxed extracts with water (aqueous) solutions of: a) citric acid, b) sodium bicarbonate, and c) brine; removing heptane from the pH-adjusted extracts by evaporation of heptane under reduced atmosphere; addition of a catalytic amount of elemental sulfur and one or more of the components found in a fire retardant, including, but not limited to, PHOS-CHEK®, or a catalyst composition based on a fire retardant, to the extracts (if not already present in the extracts); thorough purging of atmospheric gasses, including oxygen, and replacement of atmospheric gasses purged from extracts with argon or other inert gas such as nitrogen; heating of extracts under a standard pressure of inert gas at a predetermined temperature and time to allow for the isomerization of Δ9-THC to Δ10-THC and notably to minimize the dehydrogenation of THC isomers to cannabinol (CBN); lowering the temperature needed for isomerization to temperatures appropriate for vacuum distillation of cannabinoids present while still under inert atmosphere; vacuum distillation of the extracts at a predetermined temperature range and with vacuum level in the range of 0.25-10 microns Hg; collecting the distillate and redistilling it a number of times to acquire a final distillate that contains between 60% and 95% Δ10-THC; and dissolving the final distillate in n-pentane for purification of the Δ10-THC by crystallization to a purity level of 99% or greater.

In another embodiment of the present invention, a crystallization method for purification of Δ10-THC from a distillate to a purity level of 99% or greater is disclosed. The method includes the steps of: dissolving the distillate in n-pentane (2:1 dilution) into a first apparatus having an initial temperature of approximately 20° C., thereby enabling the Δ10-THC to be fully solvated for subsequent and selective crystallization from cold n-pentane solution; decreasing the temperature of the n-pentane solution by 1° C. every 2 minutes, until reaching −20° C.; allowing the chilled solution to sit undisturbed for 24 hours to enable thorough and selective precipitation of Δ10-THC as a microcrystalline solid; and filtering and washing the isolated Δ10-THC with −50° C. n-pentane to remove non-crystalline contaminants such as Δ9-THC.

The present invention is also directed to optimal extraction methods, post-extraction pH adjustments of extracts by washing extracts with aqueous solutions of acids and bases, distillation heats and times, improved crystallization methods, and definitive analytical techniques, all focused on increasing the efficiency of producing Δ10-THC in purities acceptable for use as an analytical standard and/or for use in studies to determine the unique bioactivity of Δ10-THC.

DETAILED DESCRIPTION

The following detailed description is of the best currently contemplated modes of carrying out various embodiments of the invention in which said embodiments can be carried out independently and/or in combination. The description is not to be taken in a limiting sense but is made for at least the purpose of illustrating the general principles of the invention, since the scope of the invention is best defined by the appended claims.

Figure 1:
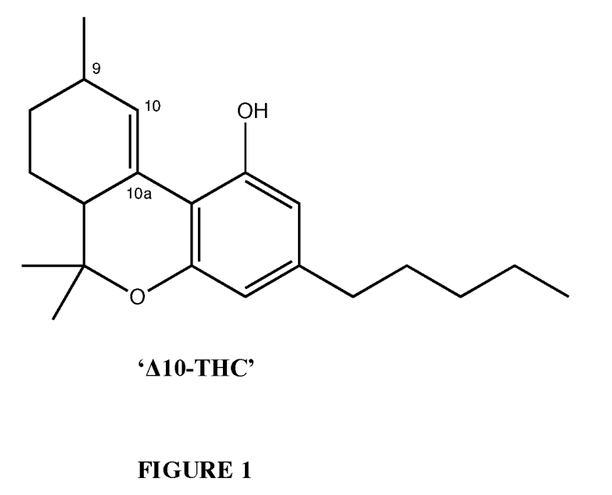
FIG. 1, represents the chemical structure of Δ10-Tetrahydrocannabinol (Δ10-THC).

FIG. 1, represents one embodiment of the chemical structure of Δ10-Tetrahydrocannabinol (THC).

Figure 2:
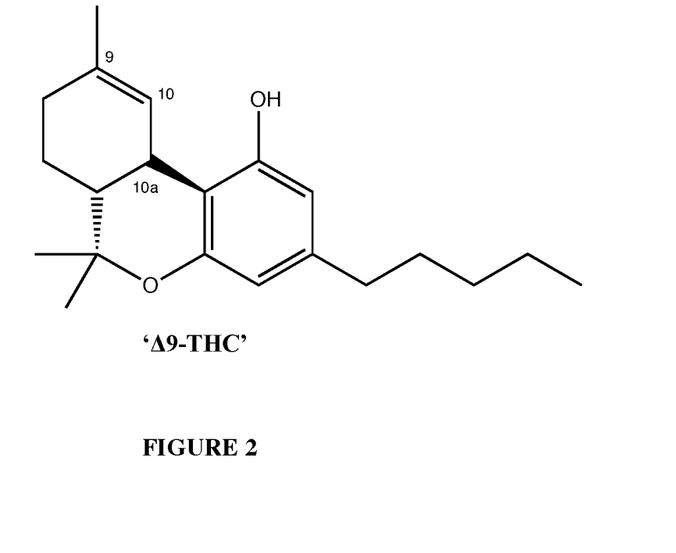
FIG. 2, represents the chemical structure of Δ9-Tetrahydrocannabinol (Δ9-THC).
Figure 3:
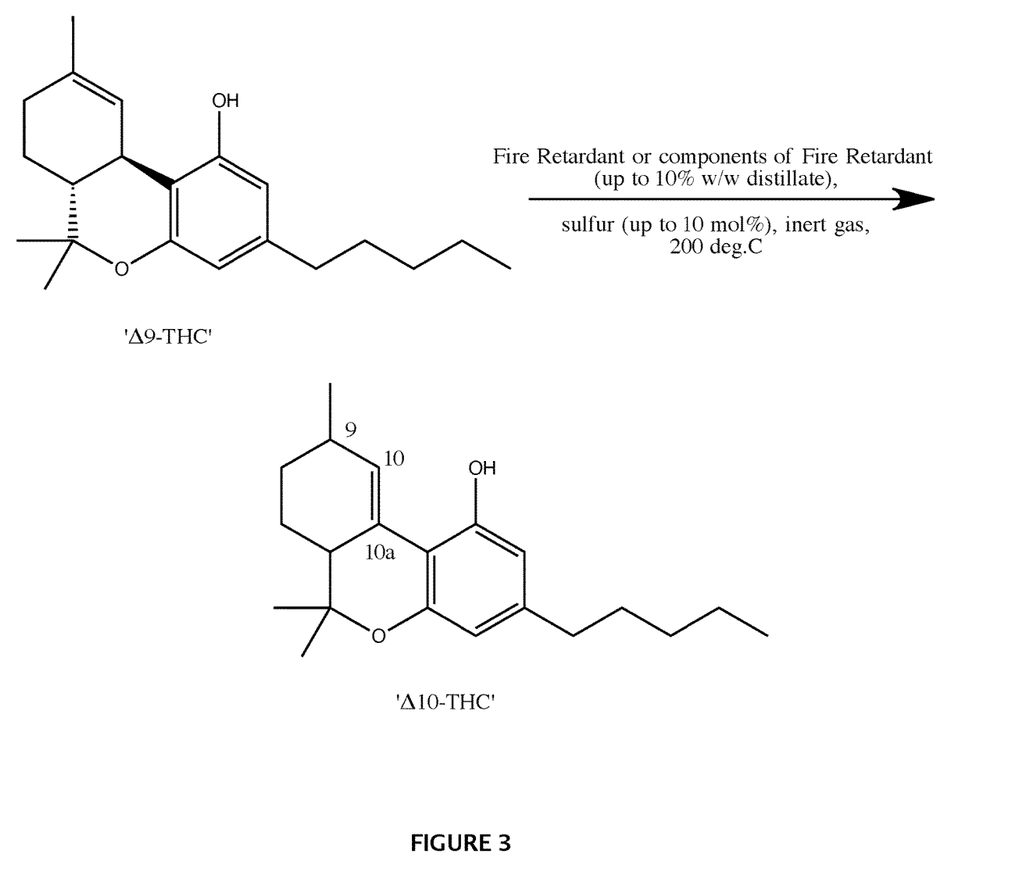
FIG. 3, represents conditions for the isomerization of Δ9-THC to Δ10-THC.

The substance identification of Δ10-Tetrahydrocannabinol (THC) includes the following:
6,6,9-Trimethyl-3-pentyl-6a,7,8,9-tetrahydro-6H-benzo[c]chromen-1-ol
(6aR-trans)-6a,7,9-tetrahydro-6,6,9-trimethyl-3-pentyl-6H-dibenzo[b,d]pyran-1-ol
(6aR-cis)-6a,7,8,9-tetrahydro-6,6,9-trimethyl-3-pentyl-6H-dibenzo[b,d]pyran-1-ol FIG. 2, represents one embodiment of the chemical structure of Δ9-Tetrahydrocannabinol (THC).

Figure 4A:
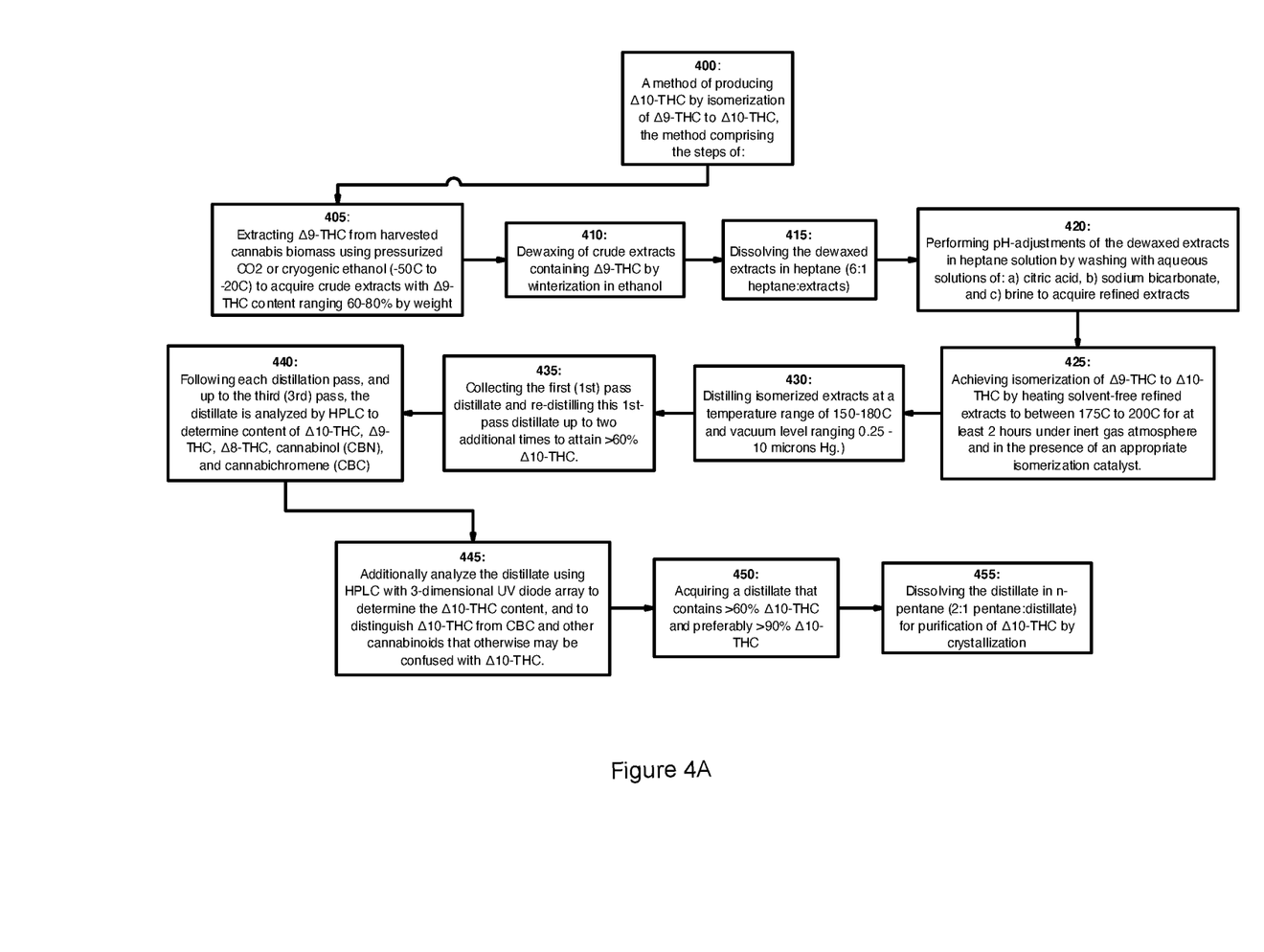
FIGS. 4A-4B represent execution diagrams for the method 400 of converting Δ9-THC to Δ10-THC and a related crystallization method 460 for purifying Δ10-THC to a purity level of 99% or greater.
Figure 4B:
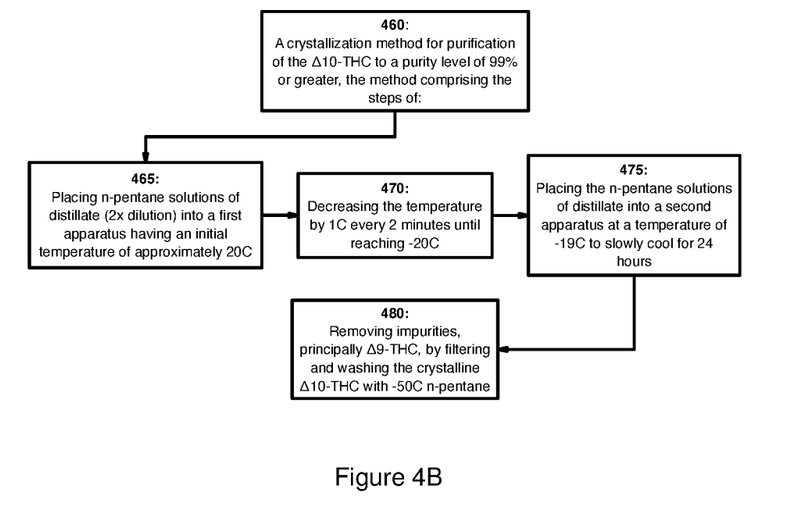

In various embodiments, cannabis extracts rich in Δ9-THC (ranging 60-80% Δ9-THC), and containing one or more of the components found in a fire retardant such as PHOS-CHEK® (as indicated by a unique, red hue present in biomass and extracts of biomass), are taken through a multi-step refining process to convert Δ9-THC to Δ10-THC as shown in FIGS. 4A-4B.

FIGS. 4A-4B represent execution diagrams for the method 400 of converting Δ9-THC to Δ10-THC and a method 460 of purifying the Δ10-THC to a purity level of 99% or greater.

At block 405, the method of the present invention comprises the step of: extracting harvested and dried cannabis biomass by either pressurized CO2 or cryogenic (−50° C. to −20° C.) ethanol to attain a crude extract, wherein the biomass contains one or more of the compounds found in fire retardant. At block 410, the crude extracts, containing 60%-80% Δ9-THC, are dewaxed by winterization in ethanol solution (a known process), followed by removal of ethanol by rotary evaporation, to provide a dewaxed extract.

At block 415 the method comprises the step of: dewaxed extracts are dissolved in heptane (6:1 heptane:extracts) and at block 420, the method includes the step of: washing with aqueous solutions (3× washes for each solution, 3:1 aqueous:heptane volume ratios) of a) citric acid (25 g citric acid per 4 L distilled water), b) sodium bicarbonate (25 g NaHCO₃ in 4 L distilled water), and brine (saturated sodium chloride solution), after which removal of heptane solvent provides a refined extract, which is followed by the step at block 425.

At block 425, the method comprises the step of: achieving isomerization of Δ9-THC to Δ10-THC by heating refined extracts containing up to 10% by weight of the fire retardant such as PHOS-CHECK®, or one or more components identified as active catalysts from the composition of the fire retardant (for example, ferric or ferrous oxides in combination with monoammonium phosphate, diammonium phosphate, ammonium polyphosphate or ammonium tripolyphosphate, attapulgus clay or equivalent clay such as Fuller's Earth or calcium bentonite, and lesser amounts of elemental sulfur), to temperatures ranging from 175° C. to 200° C. for a period of time ranging 2-3 hrs under inert gas atmosphere and with sufficient agitation to enable thorough distribution of catalyst components throughout the heated extracts.

In various embodiments, the catalyst (e.g., fire retardant) of the present invention is comprised of ferrous oxide (25 weight %), ammonium or sodium tripolyphosphate (25 weight %), attapulgus clay (25 weight %), calcium bentonite (25 weight %), and the total weight of the catalyst composition amounts up to 10 weight percent of the refined extract to be isomerized.

In other embodiments, the catalyst includes compounds selected from the group of ferrous oxide, ferric oxide, monoammonium phosphate, diammonium phosphate, ammonium tripolyphosphate, and attapulgus clay.

In further embodiments, elemental sulfur is added to the catalyst composition in an amount ranging up to 10 mol % (or up to 1 weight %) of the Δ9-THC to be isomerized to Δ10-THC.

At block 430, the method comprises the step of distilling isomerized extracts rich in MO-THC at a temperature range of 150–180° C. and vacuum level ranging from 0.25-10 microns Hg over the course of 3-5 hrs (distillation performed either by short-path distillation, spinning-band distillation, or other suitable vacuum distillation method.) In one embodiment, residual Δ9-THC was not fully separable from Δ10-THC by vacuum distillation, which required the development of crystallization methods for separation of Δ10-THC (crystalline) from Δ9-THC (not crystalline, see below.)

At block 435, the method comprises the step of: the '1ˢᵗ Pass distillate' is collected and analyzed by an appropriate analytical method, such as High-Performance Liquid Chromatography ("HPLC") for determining Δ10-THC content, and, if necessary for full isomerization of Δ9-THC to Δ10-THC, isomerized and redistilled up to two additional times using the same parameters as in block 430, for which the procedure may include additions of fresh isomerization catalyst and exposure to isomerization conditions as described above, followed by vacuum distillation under similar conditions of time, temperature and vacuum levels as described above.

At block 440, the method comprises the step of: following each distillation pass, and up to the 3ʳᵈ distillation pass, the distillate is analyzed by HPLC to determine the content of Δ10-THC, Δ9-THC, Δ8-THC, cannabinol (CBN), and cannabichromene (CBC).

At block 445, the method comprises the step of: Additionally, the distillate containing Δ10-THC is analyzed using reverse-phase HPLC, and utilizing a 3-dimensional multi-wavelength mapping of UV-absorption ('3D HPLC'), wherein the continuous scanning for absorbance between 190 nm and 400 nm enabled distinguishing Δ10-THC from cannabichromene (CBC), cannabicyclol (CBL), cannabinol (CBN), and other cannabinoids that may have similar HPLC retention times and single-wavelength absorbance of ultra-violet (UV) light, and that may otherwise be easily confused with Δ10-THC when not using 3D-HPLC detection. Common HPLC methods used for the analysis of cannabinoids utilize UV detectors or software with single-wavelength absorption, and therefore cannot easily distinguish Δ10-THC from CBC or other cannabinoids that elute at similar retention times from a HPLC column. Because Δ10-THC contains a styrenic chromophore that is significantly different in its 3D-HPLC UV absorption spectrum as compared to other cannabinoids, analysis by 3-dimensional multi-wavelength mapping of UV-absorption by a HPLC diode array detector is an appropriate tool for identifying Δ10-THC.

At blocks 450-455, the method comprises the steps of: once distillate is acquired that contains >60% Δ10-THC (and preferably >90% Δ10-THC), the distillate is dissolved in n-pentane (2:1 pentane:distillate) for purification of Δ10-THC by crystallization.

The following, as shown in FIG. 4B, is a summary of the development of an effective crystallization method 460 for purification of the Δ10-THC>99%: Initially, n-pentane solutions of distillate (2× dilution) were placed into a first apparatus such as a lab refrigerator for 2 hours at 0° C., then into a second apparatus such as a deep cryogenic freezer (−86° C.) for 24 hours. This produced a congealed white/yellow solid that was filtered and rinsed with cold n-pentane (−60° C.) to "wash out" any remaining Δ9-THC. However, purities of Δ10-THC were only 95%-98%, which could be improved upon. An improved method includes the steps of: [465] dissolving the distillate in n-pentane (2× dilution) into a first apparatus having an initial temperature of approximately 20° C., thereby enabling the Δ10-THC to be fully solvated for subsequent and selective crystallization from n-pentane solution; [470] slowly decreasing the temperature by 1° C. every 2 minutes, until reaching −20° C.; [475] allowing the chilled solution to sit undisturbed for 24 hours at −20° C. to enable thorough and selective precipitation of Δ10-THC as a micro-crystalline solid; and [480] filtering and washing the isolated Δ10-THC with −50° C. n-pentane to remove contaminants such as Δ9-THC. The result was a much whiter precipitated solid (Δ10-THC), and with the majority of yellow Δ9-THC remaining in pentane solution not congealed with the precipitated Δ10-THC. This process resulted in 98% to >99% purified Δ10-THC as an off-white solid, with the remaining 1% impurity identified by HPLC and proton ($^1$H) Nuclear Magnetic Resonance ("NMR") as Δ9-THC (See FIG. 2).

In another embodiment, further analytical techniques were used to unambiguously confirm the identity of Δ10-THC as a purified crystalline compound. Such techniques included Nuclear Magnetic Resonance ("NMR") spectroscopy, both single nucleus scans for proton ($^1$H) and carbon 13 ($^{13}$C), and multi-dimensional scans including Correlation Spectroscopy (COSY), Nuclear Overhauser Effect Spectroscopy (NOESY), Heteronuclear Multiple Bond Correlation Spectroscopy (HMBC), and Heteronuclear Single-Quantum Correlation spectroscopy (HSQC.) Notably, in the simplest demonstration of the utility of these techniques for confirming the structure of Δ10-THC, HSQC NMR (with CHCl$_3$ peak calibrated to 7.27 ppm in $^1$H NMR, and with CHCl$_3$ ranging 76.81 ppm to 77.32 ppm in $^{13}$C NMR) shows a clear correlation between the aromatic (styrenic) proton at 6.45 ppm in $^1$H NMR and carbon ten (10) at 130.24 ppm to 130.98 ppm in $^{13}$C NMR, with atomic numbering as indicated in FIG. 1.

In another embodiment, further analytical techniques were used to further confirm the identity of Δ10-THC as a purified crystalline compound, including the use of Gas Chromatography Mass Spectrometry (GCMS), wherein the dominant fragmentation peaks at 314.24, 299.23, 271.19, 258.21, 243.19, and 231.15, were confirmation of the parent compound being Δ10-THC.

In another embodiment, a melting point was taken of the purified crystalline sΔ10-THC, indicating 121° C.

It should be understood that the foregoing relates to various embodiments of the invention and that modifications may be made without departing from the spirit and scope of the invention. It should also be understood that the present invention is not limited to the designs mentioned in this application and the equivalent designs in this description, but it is also intended to cover other equivalents now known to those skilled in the art, or those equivalents which may become known to those skilled in the art in the future.

INDUSTRIAL APPLICABILITY

The present invention pertains to the production of Δ10-THC by the isomerization of Δ9 THC to Δ10-THC, which may be of value or importance to various industries, such as analytical chemistry, the pharmaceutical, retail, food and drink (i.e., edibles), and cannabis industries.

What is claimed is:

1. A method of producing Δ10-Tetrahydrocannabinol ("Δ10-THC") by isomerization of Δ9-tetrahydrocannabinol ("Δ9-THC") to Δ10-THC, the method comprising the steps of:

extracting Δ9-THC from harvested cannabis biomass comprising a crude extract;

dewaxing the crude extract containing Δ9-THC by winterization comprising a dewaxed extract;

dissolving the dewaxed extract in a heptane solution, wherein the ratio of heptane:extract is in the range 6:1;

refining of the dewaxed extract in the heptane solution to provide a refined extract by washing the dewaxed extract with aqueous solutions of: a) citric acid, b) sodium bicarbonate, and c) brine;

removing heptane from the refined extract in the heptane solution by vacuum distillation of the heptane at temperatures of less than 100° C. to provide a concentrated refined extract;

achieving isomerization of Δ9-THC to Δ10-THC by heating the concentrated refined extract between about 175° C. and 200° C. for a period of time under inert gas atmosphere and in the presence of a catalyst to provide a 410-THC concentrate;

distilling the Δ10-THC concentrate at temperatures up to 180° C. and with an applied vacuum level in the range of 0.25 to 10 microns Hg to provide a distillate;

acquiring a final distillate that contains Δ10-THC; and dissolving the final distillate in n-pentane for purification of the Δ10-THC by crystallization.

2. The method of claim 1, wherein the crude extract of cannabis biomass contains Δ9-THC in the range of 60 to 80%.

3. The method of claim 2, wherein the Δ9-THC is extracted from the biomass using pressurized CO2, or chilled ethanol in the temperature range of −50° C. to −20° C.

4. The method of claim 1, wherein the isomerization of Δ9-THC to Δ10-THC is achieved by reaction of the Δ9-THC with the catalyst, the catalyst being comprised of fire retardant and having elemental sulfur as an additive in amounts up to 10 mole-percent of the Δ9-THC present and at a temperature between about 175° C. to 200° C. and under inert gas for at least two hours, and followed by vacuum distillation of the isomerized extract at temperatures up to 180° C. and with a vacuum level of 0.25-10 microns Hg, is carried out at a predetermined time between about 1 hour to 3 hours.

5. The method of claim 1, wherein the isomerized extract having less than 60% Δ10-THC is fractionally distilled up to three (3) times to achieve enrichment of Δ10-THC of at least 60% in the final distillate.

6. The method of claim 5, wherein the final distillate is analyzed by a High-Performance Liquid Chromatography (HPLC) method comprised of scanning wavelengths in the range between 190 nm and 400 nm to generate a 3-dimensional multi-wavelength map of spectral absorption (3D-HPLC) to identify and quantify cannabinoids contained in the final distillate.

7. The method of claim 1, wherein the final distillate acquired is comprised of Δ10-THC in the range of 60% to 90% or greater.

8. The method of claim 1 further including the steps of:
dissolving the final distillate in n-pentane in a ratio ranging from 1:1 to 5:1 pentane:distillate into a first apparatus having an initial temperature of approximately 20° C.;
decreasing the temperature of the first apparatus by 1° C. every 2 minutes, until reaching −20° C.;
placing the n-pentane solutions of the final distillate into a second apparatus having an initial temperature of −19° C. to cool said n-pentane solution of the final distillate for 24 hours; and
filtering and washing a precipitated, micro-crystalline Δ10-THC with −50° C. n-pentane to wash away non-crystalline impurities.

9. The method of claim 1, wherein the extracts from the harvested cannabis biomass include fire retardant, and where the fire retardant is present in the extracts prior to isomerization in amounts ranging up to 10% by weight of the extracts.

10. The method of claim 1, wherein the step of refining the dewaxed extract is further comprised of washing the dewaxed extract in the heptane solution with aqueous solutions comprised of three (3) washes for each solution of: a) the aqueous citric acid solution being comprised of 25 g citric acid per 4 L distilled water, b) the aqueous sodium bicarbonate solution being comprised of 25 g $NaHCO_3$ in 4 L distilled water, and c) the brine being comprised of saturated aqueous NaCl solution in distilled water, wherein the ratio of aqueous:heptane is in the range of 3:1.

11. The method of claim 1, wherein the vacuum distillation that follows the isomerization is carried out by short-path distillation or spinning-band distillation.

12. The method of claim 1 further comprising the steps of:
collecting a first-pass of the Δ10-THC distillate and redistilling said Δ10-THC distillate up to three times to achieve at least 60% Δ10-THC in the final distillate, wherein after each pass the Δ10-THC distillate is analyzed to determine the content of Δ10-THC; and
analyzing the Δ10-THC distillate using High-Performance Liquid Chromatography (HPLC) having a detector and software capable of mapping the total UV diode array scan into a 3-dimensional spectral map comprised of wavelengths in the range between 190 nm to 400 nm, to determine the content of Δ10-THC and to distinguish Δ10-THC from cannabichromene (CBC) and cannabicyclol (CBL) and other cannabinoids that otherwise may be confused with Δ10-THC when using single-wavelength UV detection.

13. The method of claim 1, wherein the final distillate contains at least 60% Δ10-THC.

14. The method of claim 1, wherein the ratio of the pentane:distillate is in the range 2:1 when the final distillate is dissolved in the n-pentane for purification of the Δ10-THC by crystallization.

15. The method of claim 1 further comprising the steps of:
dissolving the distillate in n-pentane solutions of distillate, wherein the solvation ratio ranges from 1:1 to 5:1 pentane:distillate, into a first apparatus having an initial temperature of approximately 20° C.;
decreasing the temperature by 1° C. every 2 minutes, until reaching −20° C.;
placing the n-pentane solutions of distillate into a second apparatus having an initial temperature range of −19° C. to slowly cool for 24 hours; and
filtering and washing the isolated Δ10-THC with −50° C. n-pentane, thereby enabling the Δ10-THC to be purified by crystallization to purity level of 99% or greater.

16. The method of claim 6, wherein the HPLC method is used to distinguish Δ10-THC from Δ9-THC, Δ8-THC, cannabinol (CBN), cannabichromene (CBC), and cannabicyclol (CBL).

17. A method of producing Δ10-Tetrahydrocannabinol ("Δ10-THC") by isomerization of Δ9-tetrahydrocannabinol ("Δ9-THC") to Δ10-THC, the method comprising the steps of:
extracting Δ9-THC from harvested cannabis biomass to produce a crude extract;
dewaxing the crude extract containing Δ9-THC by winterization to produce a dewaxed extract;
dissolving the dewaxed extract in a heptane solution, wherein the ratio of heptane:extract is in the range 6:1 when dissolving the dewaxed extract in the heptane solution;

refining the dewaxed extract in the heptane solution to provide a refined extract by washing the dewaxed extract with aqueous solutions of: a) citric acid, b) sodium bicarbonate, and c) brine;

removing heptane from the refined extract in the heptane solution by vacuum distillation of the heptane at temperatures of less than 100° C. to provide a concentrated refined extract;

achieving isomerization of Δ9-THC to 410-THC by adding a catalyst to the concentrated refined extract and heating the mixture of the concentrated refined extract and catalyst between about 175° C. and 200° C. for a period of time under inert gas atmosphere to provide a Δ10-THC concentrate, wherein the catalyst present in the concentrated refined extract is in an amount ranging up to 10% by weight of the concentrated refined extract;

distilling the Δ10-THC concentrate at temperatures up to 180° C. and with an applied vacuum level in the range of 0.25 to 10 microns Hg to provide a distillate;

acquiring a final distillate that contains Δ10-THC; and dissolving the final distillate in n-pentane for purification of the Δ10-THC by crystallization.

18. The method of claim 17, wherein the catalyst is comprised of ferrous oxide (25 weight %), ammonium or sodium tripolyphosphate (25 weight %), attapulgus clay (25 weight %), calcium bentonite (25 weight %), and wherein the total weight of the catalyst composition amounts up to 10 weight percent of the refined extract to be isomerized.

19. The method of claim 18, wherein elemental sulfur is added to the catalyst composition in an amount ranging up to 10 mol % (or up to 1 weight %) of the Δ9-THC to be isomerized to Δ0-THC.

20. The method of claim 17, wherein the step of refining the dewaxed extract is further comprised of washing the dewaxed extract in the heptane solution with the aqueous solutions comprised of three (3) washes for each solution of: a) the aqueous citric acid solution being comprised of 25 g citric acid per 4 L distilled water, b) the aqueous sodium bicarbonate solution being comprised of 25 g NaHCO$_3$ in 4 L distilled water, and c) the brine being comprised of saturated aqueous NaCl solution in distilled water, wherein the ratio of aqueous:heptane is in the range of 3:1.

21. The method of claim 4, wherein the fire retardant includes compounds selected from the group consisting of ferrous oxide, ferric oxide, monoammonium phosphate, diammonium phosphate, ammonium tripolyphosphate, attapulgus clay, and further including the step of adding elemental sulfur in amounts ranging up to 10 mol % of the Δ9-THC to be isomerized to Δ10-THC.

* * * * *